United States Patent [19]
Burns

[11] Patent Number: 5,395,387
[45] Date of Patent: Mar. 7, 1995

[54] LANCET BLADE DESIGNED FOR REDUCED PAIN

[75] Inventor: James A. Burns, Elizabeth, N.J.

[73] Assignee: Becton Dickinson and Company, Franklin Lakes, N.J.

[21] Appl. No.: 23,496

[22] Filed: Feb. 26, 1993

[51] Int. Cl.[6] ............................................. A61B 17/32
[52] U.S. Cl. ................................................... 606/181
[58] Field of Search ............................... 606/181–185; 128/637, 770

[56] References Cited

U.S. PATENT DOCUMENTS

| | | | |
|---|---|---|---|
| 3,712,293 | 1/1973 | Mielke, Jr. | 606/182 |
| 4,535,769 | 8/1985 | Burns. | |
| 4,577,630 | 3/1986 | Nitzsche et al. | |
| 4,616,649 | 10/1986 | Burns. | |
| 4,712,548 | 12/1987 | Enstrom. | |
| 5,133,730 | 7/1992 | Biro et al. | 606/182 |
| 5,211,652 | 5/1993 | Derbyshire | 606/182 |

Primary Examiner—Stephen C. Pellegrino
Assistant Examiner—William W. Lewis
Attorney, Agent, or Firm—Alan W. Fiedler

[57] ABSTRACT

A lancet assembly having a blade designed for reduced pain that is used for piercing a patient's skin to cause capillary blood to flow for collection and testing. The blade has a shear percentage greater than conventional lancet blades to provide additional cutting action when the blade is being inserted into a puncture wound and a blade width smaller than conventional lancet blades. Reduced width and increased shear percentage result in reduced skin tear and penetration force, which therefore causes less pain to the patient during skin penetration.

20 Claims, 3 Drawing Sheets

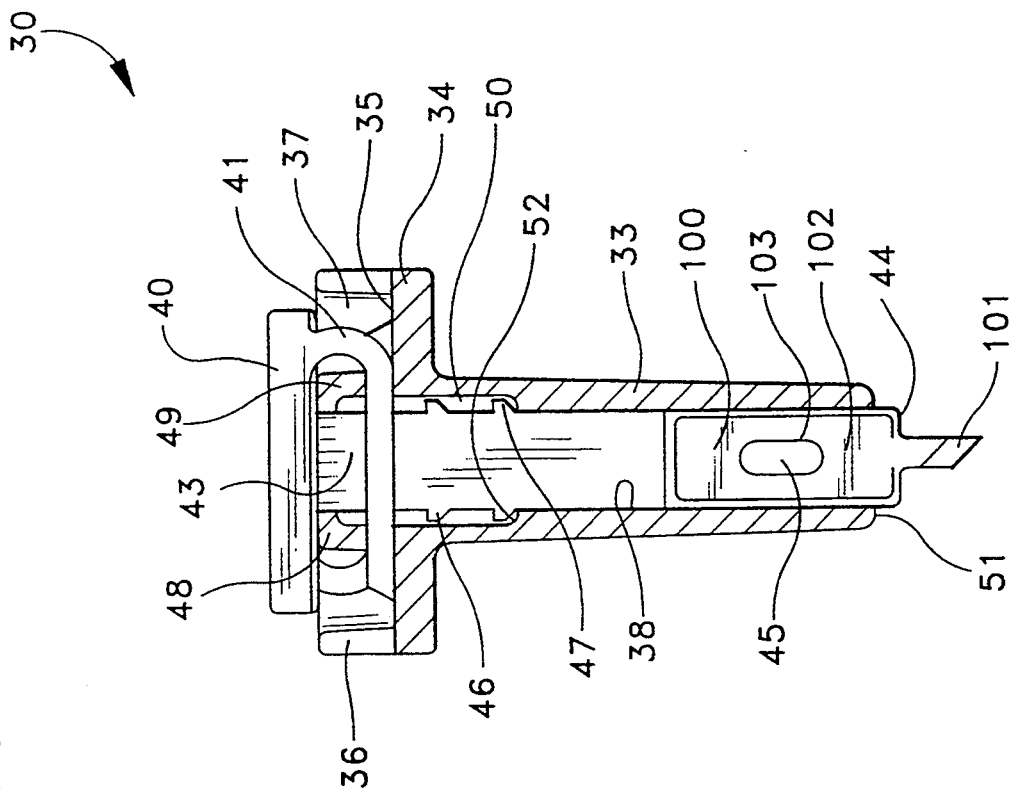
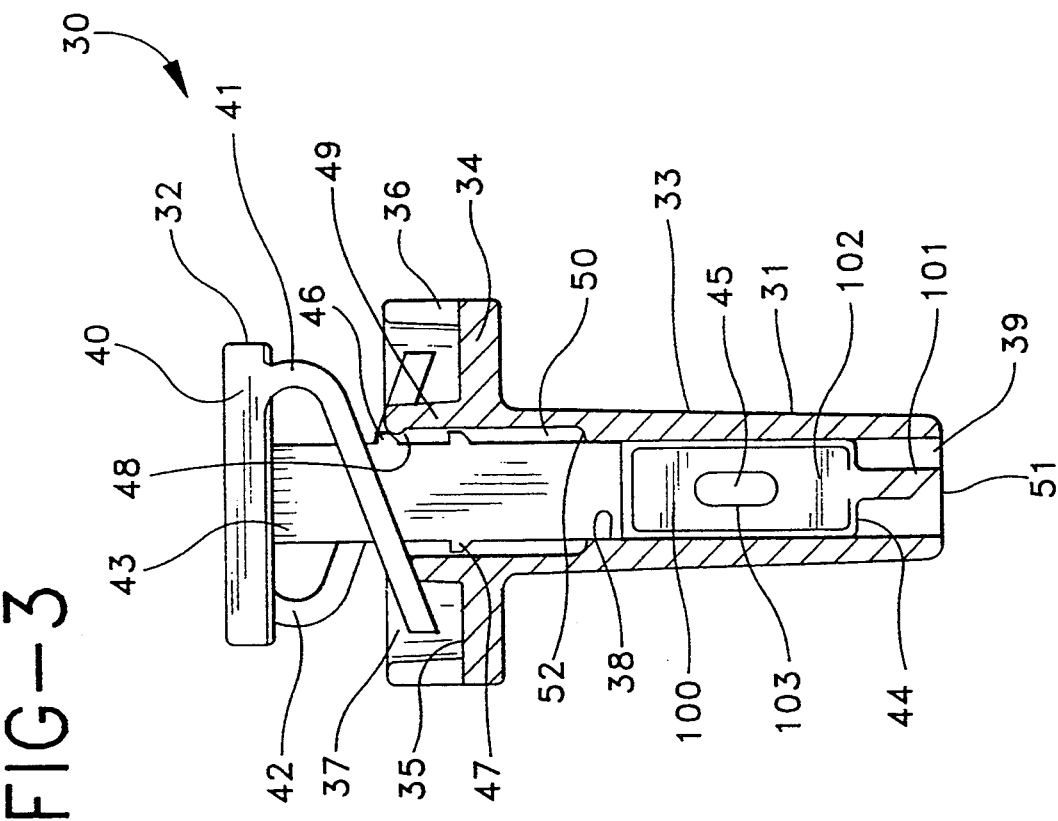

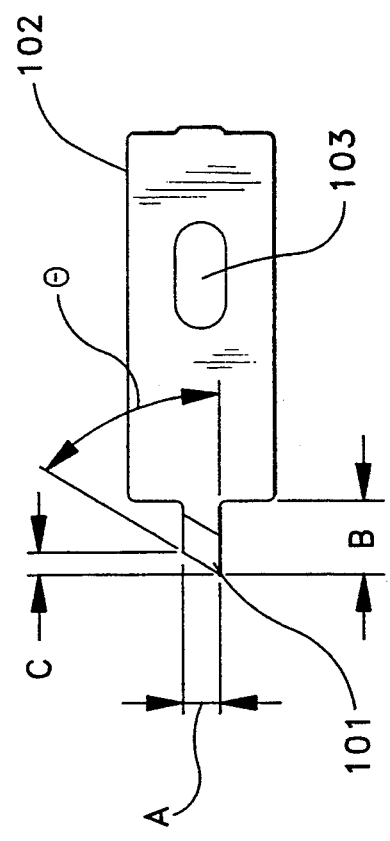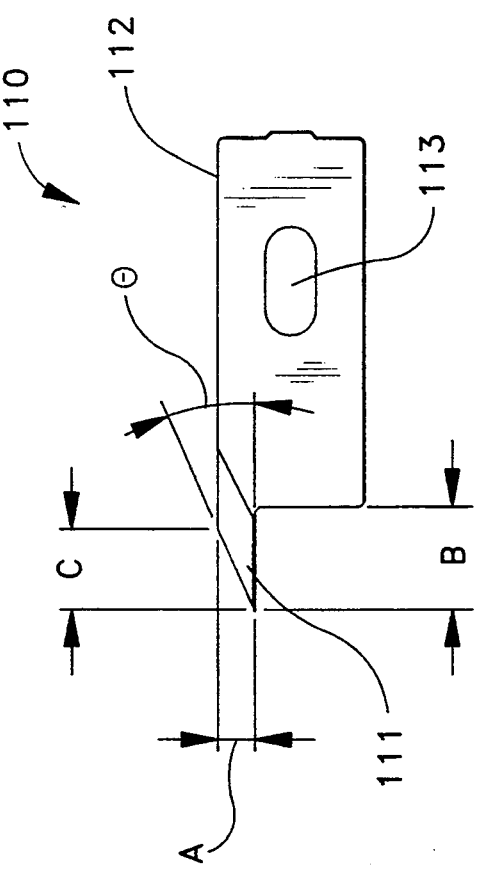

LANCET BLADE DESIGNED FOR REDUCED PAIN

BACKGROUND OF THE INVENTION

1. Field of the Invention

The present invention relates to a blade for a lancet and, more particularly, relates to a lancet blade designed for reducing the amount of pain inflicted when being used to draw blood from a patient for diagnostic testing.

2. Background Description

A lancet is a device commonly used in hospitals, doctors offices and homes to pierce a patient's flesh to draw capillary blood for diagnostic testing. Conventional lancets consist of a shank portion having at a distal end a blade or spike, which is sharp and adapted to pierce the patient's skin so to sever capillaries and provide blood for testing. Since the blade or spike is sharp, some lancets are provided with a removable shield for protectively covering the sharp edge or point of the lancet's blade or spike when not in use to protect the patient and users from inadvertent skin puncture.

FIG. 1 is a perspective view of a conventional lancet assembly 10 described in U.S. Pat. No. 4,577,630 (Nitzsche et al), which is assigned to Becton, Dickinson and Company. Lancet assembly 10 includes a handle portion 11, a spike 12 extending outwardly from a distal end 13 and a removable shield 14 adapted to mate with spike 12 when the lancet is not in use and protect users from accidental puncture. Spike 12 in lancet assembly 10 can also be replaced with a conventional lancet blade, like that shown in FIG. 2.

As shown in FIG. 2, conventional lancet blade 20 has an included angle $\theta$ of 60°, a blade width A of 1.1 mm, a blade length B of 1.85 mm and a shear length C of 0.635 mm. In addition, blade 20 has a shear percentage of 34%, wherein:

$$\text{SHEAR PERCENTAGE} = \frac{\text{SHEAR LENGTH } C}{\text{BLADE LENGTH } B} \qquad (1)$$

An example of a conventional lancet assembly for holding blade 20, is described in U.S. Pat. No. 4,616,649 (Burns), assigned to Becton, Dickinson and Company, which is similar to the 6356 Lancet sold by Becton, Dickinson and Company.

A problem with the lancets described above is that during penetration the blade or spike initially cuts but then tears sensitive nerve endings where the puncture wound is made in a finger, which causes a significant amount of pain to the patient. When using blade 20 shown in FIG. 2, the skin is cut by a shearing action over the shear length C of the blade. However, after the shearing portion of the blade has been fully inserted into the puncture wound, the blade continues to enter the skin without any cutting action being performed by the blade. Since the thickness of blade 20 continues to increase beyond the sheared portion, additional blade thickness is forced into the puncture wound thus causing tearing of the skin, which results in increased pain to the patient. Such pain to the patient is very severe since the nerve endings in the finger are very sensitive.

SUMMARY OF THE INVENTION

The present invention overcomes the problems identified in the background material by providing a lancet having a blade designed for reduced pain and reduced penetration force. In a preferred lancet blade according to present invention, the blade has a decreased width and an increased shear percentage from conventional lancet blades. In addition, the lancet blade of the present invention has a cross-sectional thickness that approaches a maximum thickness close to the junction of the blade portion and the base portion, which enables the blade to perform additional cutting action as the blade is being inserted in the puncture wound and reduce skin tear.

An alternative embodiment of a lancet blade according to the present invention has a decreased width and a blade length A equal to shear length C to provide a shear percentage of 100%. A blade of this type causes even less pain to the patient since during the entire process of inserting the blade into the puncture wound cutting of the skin is performed which results in reduced skin tear. Applicant has discovered that any increase in shear percentage also decreases penetration force which likewise reduces pain to the patient.

These and other aspects, features and advantages of the present invention will become apparent from the following detailed description taken in conjunction with the accompanying drawings.

DESCRIPTION OF THE DRAWINGS

FIG. 3 is a cross-sectional view of a lancet assembly in a retracted position having a preferred blade of the present invention;

FIG. 4 is a cross-sectional view of the lancet assembly shown in FIG. 3 in an extended position;

FIG. 5 is an enlarged side view of the blade in the lancet assembly shown in FIGS. 3 and 4; and FIG. 6 is an alternative blade according to the present invention.

DETAILED DESCRIPTION

Figure 1:
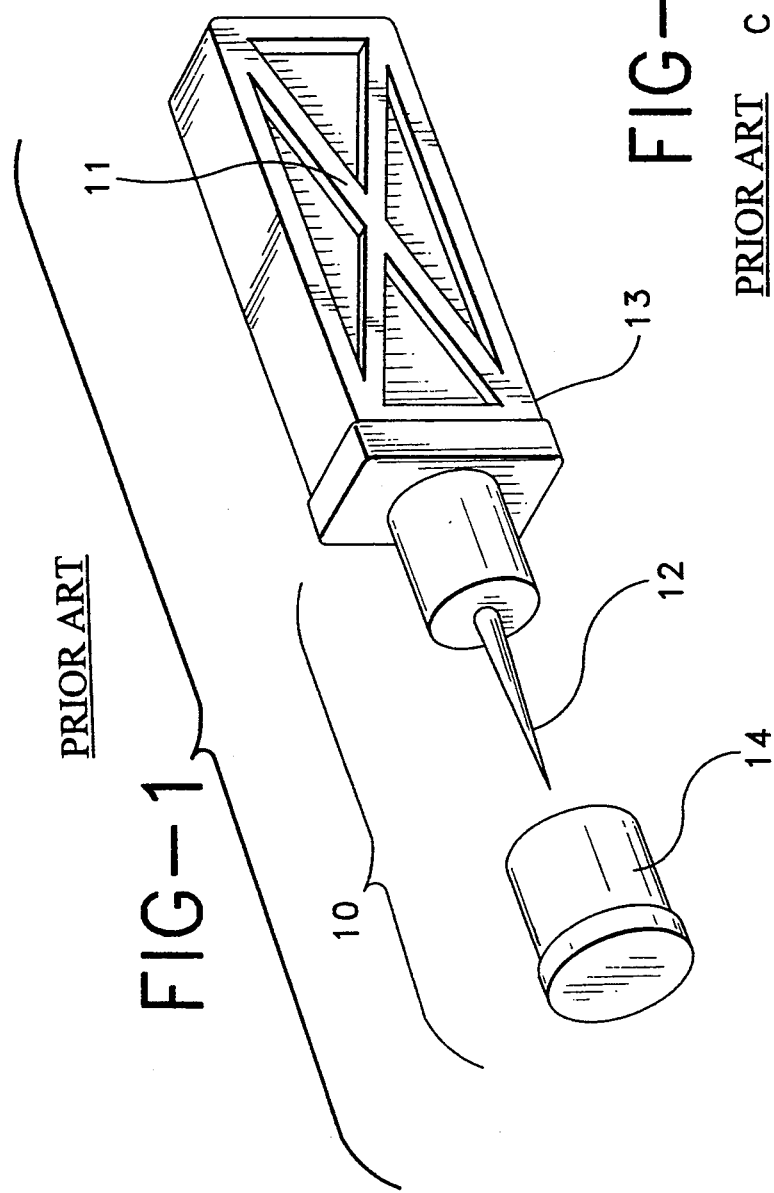
FIG. 1 is a perspective view of a conventional lancet assembly.
Figure 2:
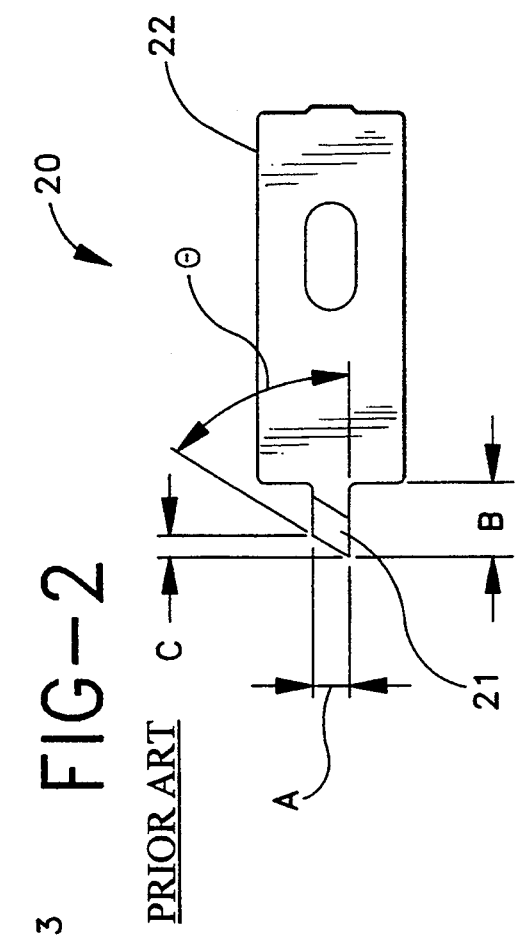
FIG. 2 is a side view of a conventional lancet blade.

FIG. 3 shows a cross-sectional view of a lancet assembly 30 that is similar to the lancet assembly described in U.S. Pat. No. 4,616,649 mentioned above. However, FIG. 3 shows a preferred blade 100 of the present invention mounted in lancet assembly 30 in place of the blade shown in U.S. Pat. No. 4,616,649.

Lancet assembly 30 shown in FIG. 3 includes a housing 31 and a slidably mounted lancet blade holder assembly 32. Housing 31 includes an elongated lower portion 33 and an upper flange portion 34 having an engaging surface 35 and an integral upwardly extending annular wall 36 which together define a space 37 for receiving a portion of lancet blade holder assembly 32. A pair of arms 49 are located within space 37 at the top of lower portion 33, each arm 49 including an integral abutment 48 extending into a passageway 39 in housing 31. Passageway 39 is defined by an internal surface 38 that extends from arms 49 in upper flange portion 34 to a lower end opening 51 at the base of lower portion 33. In operation, lancet blade holder assembly 32 is received by and travels within passageway 39. Passageway 39 also has an enlarged portion 50 in upper flange portion 34, which receives the top portion of lancet blade holder assembly 32, described below.

Lancet blade holder assembly 32 includes an integral push-button top 40 with resilient springs 41 and 42 and a shank 43 extending therefrom, shank 43 being shaped to travel through passageway 39 in housing 31 during use. Pairs of integral abutments 46 and 47 extend from opposite sides of shank 43 to cooperate with the internally extending integral abutments 48 extending from each arm 49 to control movement of lancet blade holder assembly 32 within housing 31. A boss 45 is located near a distal end 44 of shank 43 for receiving and holding blade 100 of the present invention, with boss 45 being cold staked into an opening 103 in a base portion 102 of blade 100.

Lancet assembly 30 is shown in FIG. 3 in a retracted position with a blade portion 101 of blade 100 surrounded by lower portion 33 of housing 31 and contained within lower end opening 51. In the retracted position, abutments 48 on arms 49 are engaged with abutments 46 and 47 on shank 43 which effectively holds lancet blade holder assembly 32 in a releasably fixed position within housing 31. In the position shown in FIG. 3, abutments 46 are located on the proximal side of abutments 48 which prevents shank 43 from sliding in the distal direction and provides a tactile indication to a user to indicate that lancet assembly 30 has not been used or activated. However, after the lancet assembly 30 has been used, abutments 46 are located on and abut the distal side of abutments 48, as shown in FIG. 4, with pressure being applied by compressed resilient springs 41 and 42. In the position shown in FIG. 4, the user is able to feel by the soft support under push-button top 40 that lancet assembly 30 has been used.

To use lancet assembly 30, for example, the user holds housing 31 between a thumb and third finger and holds lower end opening 51 of housing 31 in contact with the skin surface to be punctured on a patient's finger. The user then presses push-button top 40 with a second finger to force shank 43 through passageway 39 towards lower end opening 51. As force is applied to push-button top 40, abutment 46 is forced over abutment 48 which causes lancet blade holder assembly 32 to thrust forward and make an audible "snap", and project blade portion 101 beyond lower end opening 51 to puncture the patient's skin. The "snap" indicates to the user that the lancet blade is fully extended.

FIG. 4 is a cross-sectional view of lancet assembly 30 in an extended position during use after being activated, wherein blade portion 101 of blade 100 projects beyond lower end opening 51 of housing 31 and is piercing the patient's skin. In the extended position, resilient springs 41 and 42 are compressed within space 37 in upper flange portion 34 of housing 31 and abutments 48 on arms 49 are in contact with the bottom of push-button top 40, which stops distal end movement of shank 43. In this position, blade portion 101 of blade 100 will have punctured the patient's skin to begin blood flowing from capillaries in the patient's finger for testing purposes. After being activated, the user releases the pressure on push-button top 40 which allows compressed resilient springs 41 and 42 to withdraw lancet blade 100 from the puncture wound. More particularly, as pressure is released from push-button top 40 resilient springs 41 and 42 retract blade holder assembly 32 into lower end opening 51 of housing 31 so that blade portion 101 is surrounded and contained within lower portion 33 of housing 31 for disposal.

FIG. 5 is an enlarged side view of the preferred blade 100 shown in FIGS. 3 and 4. As described above, blade 100 includes blade portion 101 and base portion 102, with base portion 102 having an opening 103 for receiving boss 45 on shank 43 of lancet blade holder assembly 32. As shown in FIG. 5, blade portion 101 has a width A of 0.60 mm, a blade length B of 2.3 mm, a shear length of 0.874 mm, and an included angle $\theta$ of 45°. Using equation (1), defined above, the shear percentage for blade 100 is 38%. The inventor has discovered that increasing the shear percentage of a lancet blade, so that the blade performs more cutting action as it is piercing the patient's skin, reduces the overall penetration force needed to pierce the patient's skin thus reducing the pain that the patient feels. In addition, the inventor has discovered that reducing the width of the blade and the blade length, within reason so to avoid jeopardizing the quantity of blood flowing from the puncture, also reduces penetration force which likewise reduces pain during penetration. Blade 100 of the present invention includes a decreased blade width A of 0.60 mm and an increased shear percentage of 38%, which combined provide a lancet blade that is much improved over conventional lancet blades since it causes the patient much less pain during penetration. Of course, the above-listed dimensions are merely exemplary, other dimensions could also be used. For example, another embodiment of blade 100 could have a conventional blade length of 1.5 mm with a blade width A less than 1.1 mm, e.g., 1 mm, 0.60 mm or 0.50 mm, or a conventional blade width of 1.1 mm with an increased shear percentage up to 100%.

FIG. 6 shows an alternative embodiment of a lancet blade 110 for reduced pain, which is mountable in lancet blade assembly 30 shown in FIGS. 3 and 4 in place of blade 100. As shown, blade 110 has a base 112 with an opening 113 that receives boss 45 on shank 43 to mount and hold blade 110. Blade 110 also includes an extended blade portion 111 that is offset from the center of the longitudinal axis of blade 110. Offset blade portion 111 permits the edge of blade 110 to be easily ground to have a cutting edge with a shear percentage of 100%. In addition, blade 110 has a blade width A of 1.0 mm, a blade length B of 2.3 mm, a shear length C of 2.3 mm and an included angle $\theta$ of 25°. With a shear percentage of 100%, blade 110 continually cuts the patient's skin during penetration which causes even less pain than conventional blades. The decreased width A of 1.0 mm on blade 110 also decreases the pain caused during penetration of the patient's skin, as described above with respect to blade 100.

As for manufacturing lancet assemblies with blades 100 and 110, the blades are made of surgical steel and are cold staked onto shank 43 of lancet assembly 30 using conventional manufacturing techniques. Housing 31 and blade holder assembly 32 of assembly 30 are made of molded plastic. However, of course, these manufacturing techniques and materials are merely exemplary, various other manufacturing methods and materials could also be used.

In the foregoing discussion, it is to be understood that the above-described embodiments are simply illustrative of a lancet blade that provides a reduction in the pain inflicted on a patient when piercing the patient's skin in accordance with the present invention. Other suitable variations and modifications could be made to these embodiments and still remain within the scope of the present invention.

What is claimed is:

1. A lancet assembly comprising:
    a housing having an upper and lower end with a passageway extending from said upper end to an opening at said lower end;

a blade holder having a shank slidably received in said passageway for movement from a retracted position to an extended position; and a blade mounted on said shank having:
- (i) a base portion having a predetermined cross-sectional thickness;
- (ii) a blade portion extending from said base portion to a distal point having a blade width from a first edge to a second edge of less than 1.1 mm and a cross-sectional thickness that decreases from said base portion to said distal point; and
- (iii) a shear portion that extends across the entire blade width from said first edge to said second edge, wherein said blade portion is surrounded by said passageway when said holder is in the retracted position and extends beyond said lower end of said housing when said holder is in the extended position.

2. A lancet assembly according to claim 1, wherein said blade has a shear length and a blade length that are equal.

3. A lancet assembly according to claim 1, wherein said blade portion has a length of at least 2.3 mm.

4. A lancet assembly according to claim 3, wherein said blade is sheared along the entire length of said blade portion.

5. A lancet assembly according to claim 1, wherein said blade portion has an included angle less than 60°.

6. A lancet assembly according to claim 5, wherein said blade has a shear percentage of 100%.

7. A lancet assembly according to claim 1, wherein said blade portion has an included angle no larger than 45°.

8. A lancet assembly according to claim 1, wherein said blade width is no larger than 1 mm.

9. A lancet assembly according to claim 1, wherein said blade width is no larger than 0.60 mm.

10. A lancet assembly according to claim 1, wherein said blade has a shear percentage larger than 34%.

11. A lancet assembly according to claim 1, wherein said blade has a shear percentage of at least 38%.

12. A lancet assembly comprising:

a housing having an upper and lower end with a passageway extending from said upper end to an opening at said lower end;

a blade holder having a shank slidably received in said passageway for movement from a retracted position to an extended position; and a blade with a shear percentage larger than 34% mounted on said shank having:
- (i) a base portion having a predetermined cross-sectional thickness;
- (ii) a blade portion extending from said base portion to a distal point having a predetermined blade width from a first edge to a second edge and a cross-sectional thickness that decreases from said base portion to said distal point; and
- (iii) a shear portion that extends across the entire blade width from said first edge to said second edge, wherein said blade portion is surrounded by said passageway when said holder is in the retracted position and extends beyond said lower end of said housing when said holder is in the extended position.

13. A lancet assembly according to claim 12, wherein said blade has a shear length and a blade length that are equal.

14. A lancet assembly according to claim 12, wherein said blade portion has a length of at least 2.3 mm.

15. A lancet assembly according to claim 14, wherein said blade is sheared along the entire length of said blade portion.

16. A lancet assembly according to claim 12, wherein said blade portion has an included angle less than 60°.

17. A lancet assembly according to claim 16, wherein said blade has a shear percentage of 100%.

18. A lancet assembly according to claim 12, wherein said blade portion has an included angle no larger than 45°.

19. A lancet assembly according to claim 12, wherein said blade width is no larger than 1 mm.

20. A lancet assembly according to claim 12, wherein said blade width is no larger than 0.60 mm.

* * * * *